(12) United States Patent
Bergfalk et al.

(10) Patent No.: US 7,720,610 B2
(45) Date of Patent: May 18, 2010

(54) DETECTION OF PSYCHOLOGICAL DISORDER ACTIVITY PATTERNS

(75) Inventors: Henrik Bergfalk, Göteborg (SE); Petter Knagenhjelm, Pixbo (SE)

(73) Assignee: Qbtech AB (SE)

( * ) Notice: Subject to any disclaimer, the term of this patent is extended or adjusted under 35 U.S.C. 154(b) by 1083 days.

(21) Appl. No.: 10/529,948

(22) PCT Filed: Sep. 26, 2003

(86) PCT No.: PCT/SE03/01496

§ 371 (c)(1),
(2), (4) Date: Jun. 10, 2005

(87) PCT Pub. No.: WO2004/030538

PCT Pub. Date: Apr. 15, 2004

(65) Prior Publication Data

US 2005/0245790 A1 Nov. 3, 2005

(30) Foreign Application Priority Data

Oct. 4, 2002 (SE) .................................. 0202948

(51) Int. Cl.
*G01N 33/48* (2006.01)
(52) U.S. Cl. ...................................................... 702/19
(58) Field of Classification Search .................... 702/19
See application file for complete search history.

(56) References Cited

U.S. PATENT DOCUMENTS

| | | | | |
|---|---|---|---|---|
| 5,691,693 A | * | 11/1997 | Kithil | ........................ 340/439 |
| 5,914,394 A | | 6/1999 | Chen et al. | ................... 536/23.5 |
| 6,006,188 A | * | 12/1999 | Bogdashevsky et al. | ..... 704/270 |
| 6,070,098 A | * | 5/2000 | Moore-Ede et al. | ......... 600/544 |
| 6,090,044 A | | 7/2000 | Bishop et al. | ................ 600/300 |
| 6,241,686 B1 | | 6/2001 | Balkin et al. | ................. 600/544 |
| 6,248,063 B1 | * | 6/2001 | Barnhill et al. | .............. 600/300 |

OTHER PUBLICATIONS

Spencer et al., "Efficacy of a Mixed Amphetamine Salts Compound in Adults with Attention-Deficit/Hyperactivity Disorder," Archives of General Psychiatry (2001) vol. 58, pp. 775-782.*
International Search Report for PCT/SE03/01496 dated Dec. 15, 2003.
"A Real-time Image Analysis System for Computer-Assisted Diagnosis of Neurological Disorders" by Tan et al 1999.
"Human Gait and Posture Analysis for Diagnosing Neurological Disorders" by Lee et al., 2000.
"Design and test of neural networks and statistical classifiers in computer-aided movemnet analysis: a case study on gait analysis" by Lafuente et al., 1997.

* cited by examiner

*Primary Examiner*—Jerry Lin
(74) *Attorney, Agent, or Firm*—Ostrolenk Faber LLP

(57) ABSTRACT

A method for detecting a psychological disorder in a person comprises collecting movement and, optionally, other data from the person by a device borne by the person; storing the data in a memory in contact with the device during the collection of data; transferring the stored data to a computer; calculating at least one set of parameter data distinctive of the movement data; feeding the least one set of parameter data to an Artificial Neural Network trained to recognize in the data a feature specific for a psychological disorder or a group of such disorders. Also is disclosed an assembly for carrying out the method.

11 Claims, 1 Drawing Sheet

DETECTION OF PSYCHOLOGICAL DISORDER ACTIVITY PATTERNS

CROSS REFERENCE TO RELATED APPLICATION

The present application is a 35 U.S.C. §371 national phase conversion of PCT/SE2003/001496 filed 26 Sep. 2003, which claims priority of Swedish Application No.0202948-6 filed on 4 Oct. 2002.

The PCT International Application was published in the English language.

FIELD OF THE INVENTION

The present invention relates to a method for detecting of activity patterns in persons which are indicative of psychological disorders, in particular psychological disorders characterised by aberrant motion behaviour, such as ADHD and related disorders. The invention further relates to a means for carrying out the method.

BACKGROUND OF THE INVENTION

Most psychiatric disorders are polygenic. In addition, each gene involved in particular disorder accounts for a small portion of the variance of a particular behavioural variable. Thus the identification of genes involved in polygenic disorders of this kind and, vice versa, the diagnosis of a psychiatric disorder in a person by genetic means seems to be a most difficult task. Thus clinical diagnoses up to now have to be based on clinical observations which are, of course, quite subjective. The fact that certain psychiatric disorders such as human bipolar affective disorder (BAD) have been demonstrated to be associated with particular genes such as the fsh 16 gene (U.S. Pat. No. 5,914,394) has not substantially affected this situation.

Persons who suffer from psychological disorders often differ in their movement patterns from persons without these disorders, and also among themselves due to the nature of the respective disorder. The movement patterns of persons can be registered by various means, including actigraphs. U.S. Pat. No. 6,241,686 describes a system and a method for predicting human cognitive performance based on data recorded by an actigraph. The method calculates a numerical estimate of cognitive performance for an individual as a continuous function of time. By attributing particular movement patterns to particular psychological disorders it is possible, in principle, to identify or at least make probable the existence of a particular psychological disorder or group of psychological disorders in a person. This attribution does however not have been solved in a convenient manner up to now. The present invention seeks to remedy this deficiency.

OBJECTS OF THE INVENTION

It is an object of the invention to provide a method for detecting a psychological disorder in a person by recording an activity pattern of the person and analysing it.

It is another object of the invention to provide a means for said recording and analysis.

Further objects of the invention will be evident from the following short description of the invention, a preferred embodiment illustrated in a drawing, and the appended claims.

SUMMARY OF THE INVENTION

According to the present invention is provided a method for detecting a psychological disorder in a person by recording an activity pattern of the person and analysing it, the method comprising:
  collecting movement and, optionally, other data from a person by a device borne by the person during data collection;
  storing the collected data in a memory in contact with the device during the collection of data;
  transferring the stored data to a computer,
  calculating at least one set of parameter data distinctive of said movement data;
  feeding said at least one set of said parameter data to an Artificial Neural Network trained to recognise in said data a feature specific for a psychological disorder or a group of psychological disorders, thereby determining the presence or absence of said psychological condition.

In this application "a memory in contact with the device" relates to a memory in physical (electrical) or wireless contact with the device such as, for instance, by infrared radiation.

In this application "Psychological disorder" comprises any psychological disorder which may affect the movement pattern of a person. Psychological disorders of the invention include but are not limited to: Attention-deficit-hyperactivity disorder (ADHD), Disruptive behaviour disorder, Disorders including sleep disorders such as Primary insomnia and Sleepwalking disorder, Posttraumatic stress syndrome, phobias, Bipolar affective disorder, Bipolar mood disorder, Major depression, Unipolar major depressive disorder, Schizoaffective disorder manic type, Schizophrenia, Panic disorder with agoraphobia, Social phobia, Obsessive-compulsive disorder, Amphetamine abuse, Hallucinogen disorder, Cannabis intoxication, Opoid dependence, Tourette's Disorder, Autistic disorder. Particular preferred is the application of the method of the invention to ADHD and other hyperactivity disorder. Also preferred is the application of the method of the invention to Bipolar affective disorder (maniac-depressive illness).

In this application "movement" of the device means the passive movement of the device with the person carrying it. The device is in a fixed position. It may be fixed at the body of the person but also, for instance, at an arm or a leg of the head of the person.

It is more preferred to calculate at least two sets of parameter data.

According to a first preferred aspect of the invention it is preferred to collect non-movement data, in particular heart rate data, simultaneously with the collection of the movement data, and to analyse said other data in a corresponding manner in the artificial neural network.

According to a second preferred aspect the method of the invention is applied to a person in a normal state and in a state in which the person is under the influence of a drug which is capable of affecting a psychological disorder of which the person may suffer, such as, for instance, amphetamine or other sedative, anxiolytic or antidepressant, and to compare the results obtained. Also preferred are drugs for the treatment of bipolar affective disorder, such as lithium salts, carbamazepine and valproic acid. In a person suffering of a psychological disorder the administration of a drug effective against that disorder will tend to normalise the movement pattern whereas a drug which is not effective will not normalise the movement pattern or may make it to deviate even more from the normal. A preferred drug of the invention is amphetamine. It is preferred to administer the drug of the invention prior to or at the start of the collection (recording) of movement data. Alternatively the drug is administered during the collection of movement data. It is also preferred for the drug to be a sedative or anxiolytic or antidepressant.

According to a third preferred aspect of the invention the movement and, optionally, other data is collected over a period of at least 8 hours, in particular of at last 24 hours.

According to the present method is also disclosed of an assembly carrying out the method of the invention, the assembly comprising:

- a device for collecting movement and, optionally, other data from a person, the device being borne by the person during data collection;
- a memory in contact with the device during the collection of data for storing said data;
- transfer means including an interface for the transfer of the stored data to a computer,
- software means for calculating at least one set of parameter data distinctive of said movement data;
- means for feeding said at least one set of said parameter data to an Artificial Neural Network trained to recognise in said data a feature specific for a psychological disorder or a group of psychological disorders.

Definitions

Model. To distinguish between different signal patterns, a model is used to characterise typical qualities and features of the patient data. The model parameters are chosen with the aim to be as distinct, unambiguous and informative as possible. The set of parameters shall reflect the typical signal patterns.

While the parameters chosen are sensitive to movement and other patterns characteristic of the particular psychological condition, it is important that that they shall be substantially insensitive to features irrelevant to the task.

Feature vector. The values of the model parameters are compiled to form a vector named the feature vector. For each subset of patient data, the values of the feature vector are extracted. Each k-dimensional feature vector can be regarded as one point in a k-dimensional signal-space.

Training. An Artificial Neural Network is iteratively trained to organise groups or clusters of feature vectors with similar properties. The self-organising process, known as Self Organising Feature Map (SOFM), for example as described in T. Kohonen "Phonetic typewriter for Finnish and Japanese", has shown great capability of performing this task.

The number of clusters is defined prior to the training and is determined by the required resolution of the Artificial Neural Network. The training is initiated by a set of (for example M) clusters, randomly positioned in the k-dimensional signal-space. Compiling the feature vectors from a large number of patients forms the database used for training. During the training, each input feature vector is compared to each cluster to find the one with best resemblance to the input vector. This cluster is voted winner, and is adjusted towards the input vector. In addition, all other clusters within a neighbourhood to the winner in another domain, the so-called map-space, are adjusted towards the input vector. The map-space is usually of low dimension containing a node for each cluster in the signal-space The nodes are arranged in a hexagonal or a square lattice, and the Euclidean distance between them defines their internal relation. A node's neighbourhood is usually defined by a neighbourhood function and contains the set of all nodes at the beginning of the training, whereas only a few (or none) are considered neighbours at the end. The further away a node is to the winner in the map-space, the less the corresponding cluster in the signal-space is adjusted towards the input vector. Thus all adjustments are done in the signal-space, while the rules of adjustments are defined in the map-space.

The training time is predetermined. An annealing function is used to "freeze" the system causing only small adjustments at the end of the training. The neighbourhood function creates a correlation between the signal-space distance and the map-space distance allowing classification to be performed in the (low dimensional) map-space, rather that in the more complicated signal-space.

The method described above is known as "unsupervised learning", i.e. there is no need to use classified data in the training procedure described above.

When the Artificial Neural Network is readily trained, the clusters will represent features of the input signal including normal and aberrant types, the latter being related to psychological disorders.

The response (output) of the Artificial Neural Network is proportional to the signal distance between the input signal and all the clusters. Often this output is of less interest in the case of classification. The output is instead used to find the node with best resemblance to a classified input. This is known as the labelling phase in the design of the Artificial Neural Network. Features with known qualities are presented for the Artificial Neural Network, the output is observed and the node giving the highest output is labelled with the presented feature. The actual output thereafter is the label rather than the response value.

The set of clusters are now stored and can be later used in the analysis in runtime mode. Patient data is analysed exactly in the same way as in the training phase to extract the values of the parameters used in the model, i.e., the feature vector. The feature vector is then presented to the network, which will produce the output label (classification).

Shortly, the present invention is based on the understanding that an analysis of patient data with an Artificial Neural Network can be successfully used to distinguish between persons with psychological disorders and persons without such disorders.

Thus, the present invention provides an analytic method in which patient data, consisting of motion data and, optionally, other data such as heart rate, is used for calculation of a number of parameters. Patient data are collected from a large number of patients and the data is used to train the Artificial Neural Network to teach the system the variation ranges of the parameters. The result from the Artificial Neural Network is obtained as a low-dimensional chart in which each set of patient data is represented by a point or a trajectory. A point or a trajectory for a patient who does not suffer from psychological disorders looks different from that for a patient with psychological disorder.

The invention will now be explained in more detail by reference to a preferred embodiment illustrated in a single FIGURE.

DESCRIPTION OF A PREFERRED EMBODIMENT

EXAMPLE 1

Application to Patient Data

Figure 1:
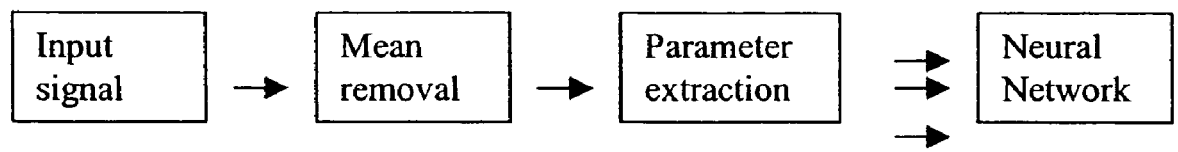
FIG. 1 is a block diagram of the system of the invention.

Equipment. A portable device such as an actigraph that can record the movement of a patient and store the movement data obtained in an internal memory. The device measures movement by an accelerometer. The measurement is performed at 10 Hz but the processed data in form of mean values are stored in intervals of one minute. The device is battery powered. Also included is dedicated software based on the method of the invention. The Artificial Neural Network has been trained with data from 100 patients. The following parameters were used in the analysis: activity profile, diurnal activity and nocturnal activity.

Patients. 20 patients aged from 6 to 12 years, some suffering from ADHD and some not.

Measurement. The patient was provided with a measurement device comprising of an actigraph in a clinic. Actigraphs which can be used in the method of the invention include but are not restricted to: ActiTrac from IM systems, Actiwatch from Mini-Mitter Co Inc, Actiwatch from Cambridge Neurotechnology and Sleep Watch from Ambulatory Monitoring Inc.

The device was attached to the patient's non-preferred arm. The patient was then sent home. The patient was instructed to wear the device during the whole measurement period of 72 hours except for time periods for bath or shower since the device way not be entirely waterproof. After the test period the patient reported to the clinic where the device was removed and the data stored in the device was transferred to a PC. The data was analysed with software according to the invention. The analysis was able to distinguish between patients with ADHD and patients without ADHD.

EXAMPLE 2

Implementation

Data acquisition. Reference is made to FIG. 1. Let the input signal(s) be a digitised version of the measured signal(s). Each signal is sampled at certain rate, giving a sequence of samples $$x_t, t=0, 1, \ldots, N$$

Pre-processing. The raw data can be processed with mean function and a factor L.

$$\bar{x}_i = \frac{1}{L}\sum_{j=0}^{L}(x(i*L+j)), i = 0, 1, 2, \ldots N/L$$

Parameters. A window is used to calculate parameters on a subset of the data at a time. The window is then slid over the entire measurement. The parameters extracted may be one or more, but not limited to the following.

The variance of motion data defined as $$\frac{1}{N-1}\sum_{i=1}^{N}(a_i - \bar{a})^2,$$

where, a, is the acceleration force at sample i and $$\bar{a} = \frac{1}{N}\sum_{i=1}^{N}a_i$$

i.e. the mean acceleration force.

Activity profile that describes relationship between low and high activity periods;

An estimate of low activity periods;

Circadian acrophase profile: a parameter describing biologic day/night rhythms;

Diurnal activity;

Nocturnal activity.

The variance of heart rate data defined as $$\frac{1}{N-1}\sum_{i=1}^{N}(h_i - \bar{h})^2,$$

where, h, is the heart rate at sample i and $$\bar{h} = \frac{1}{N}\sum_{i=1}^{N}h_i$$

i.e. the mean heart rate.

Correlation between activity and heart rate.

Feature Map Geometry and Definitions

Let the M k-dimensional map nodes be denoted $$m_i, i=0, \ldots, M-1$$

Most often the nodes are arranged in a square (2-dimensional) grid. The distance between two map nodes i and j, is denoted $D_{i,j}$ and defined as the squared Euclidean distance ($L^2$ norm) between them in the map-space.

$$D_{i,j}=L^2(m_i,m_j)$$

This measure is used in the neighbourhood function.

Let the input feature vector, representing sample $x_n$ be denoted $y_n$. Furthermore, let the map response in node i for feature n, $S_{i,n}$ be defined as:

$$S_{i,n}=e^{-(d_{i,n}^2/k)}$$

where the signal-space distance $d_{i,n}^2$ is defined as $$d_{i,n}^2 = \sum_{i=1}^{k}w_l(y_l^n - m_l^i)^2$$

and $w_i$ is some suitable weight function.

Annealing function. The task of the annealing function is to obtain equilibrium at the end of the training. The principle is that large adjustments are allowed in the beginning of the training whereas only small (or zero) adjustments are allowed at the end. How the decrease incorporated is not critical. Linear, exponential, and even pulsating [3] decay schedules are proposed in the literature.

Initialisation. Traditionally, all data driven clustering schemes, including Artificial Neural Network, employ random positioning of clusters in the signal-space, by assigning (small) random numbers to the parameters. The actual values are not important as long as they are not identical. The ordering of the clusters is also at random.

Training. The iteractive algorithm adjusts all clusters after each input feature vector, $y_n$ presented, the direction of the adjustment is towards $y_n$ and how much is determined partly by the annealing function, partly by the neighbourhood function. The adjustment formulae for cluster $m_i$ at time instant $t+1$ is;

$$m_i(t+1) = m_{i(t)} + \gamma_i(t)*(y_n - m_i(t)), i=0, \ldots, M-1$$

where $$\gamma_k(t) = f(t)*g(t),$$

and $f(t)$ is the annealing function and $g(t)$ is the neighbourhood function. Various suitable functions are discussed in P. Knagenhjelm, "A recursive design method for Robust Vector Quantization".

The invention is not limited to the illustrated and described embodiments. Variations and modifications may occur within the scope of the attached claims.

The invention claimed is:

1. A method for detecting a psychological disorder condition in a person by recording an activity pattern of the person and analyzing the pattern, the method comprising:
   receiving, by an electronic memory, electronic activity data comprising at least electronic movement data, wherein the electronic movement data are received from a movement measuring device, and further wherein the electronic movement data are collected by the movement measuring device while the device is worn by the person;
   storing the collected activity data in a database that is accessible by
   a computer;
   calculating by the computer at least one set of parameter data distinctive of the electronic movement data;
   feeding the at least one set of parameter data to an Artificial Neural Network;
   organizing, by the Artificial Neural Network, groups or clusters of the parameter data that have similar properties, wherein the properties represent a feature specific for a psychological disorder or a group of psychological disorders;
   associating the groups or clusters with labels dependent on features from the parameter data having known qualities that are related to psychological disorders;
   analyzing, by the Artificial Neural Network, the received set of parameter data by:
   (i) determining, dependent on the set of parameter data, a response value that is indicative of a distance between the received set of parameter data and the groups or clusters; and
   (ii) determining, dependent on the response value, at least one of the groups or clusters that is proximate to the response value; and
   outputting an indication of the label of the at least one of the groups or clusters as a classification of a respective feature related to at least one psychological disorder, thereby determining the presence or absence of the psychological condition.

2. The method of claim 1, wherein the psychological disorder is Attention-deficit-hyperactivity disorder (ADHD).

3. The method of claim 2, wherein the psychological disorder is ADHD and other hyperactivity disorder.

4. The method of claim 1, further comprising calculating at least two sets of parameter data.

5. The method of claim 1, further comprising collecting by the device non-movement data simultaneously with the movement data; and
   analyzing the non-movement data in a corresponding manner in the artificial neural network.

6. The method of claim 5, wherein the non-movement data are heart rate data.

7. The method of claim 1, wherein the person is under the influence of a drug capable of affecting a psychological disorder of which the person may suffer during the collecting of the movement data.

8. The method of claim 7, wherein the drug is amphetamine.

9. The method of claim 1, wherein movement data are collected over a period of at least 8 hours.

10. The method of claim 1, wherein movement data are collected over a period of at least 24 hours.

11. An assembly for detecting a psychological disorder condition in a person by recording an activity pattern of the person and analysing it, the assembly comprising:
    a device for collecting movement and, optionally, other data from a person, the device being borne by the person during data collection;
    a memory in contact with the device during the collection of data for storing the data;
    transfer means including an interface for the transfer of the stored data to a computer,
    software means for calculating at least one set of parameter data distinctive of the movement data;
    means for feeding the at least one set of the parameter data to an Artificial Neural Network configured to recognize in the data a feature specific for a psychological disorder or a group of psychological disorders by organizing groups or clusters of the parameter data having similar properties and representing features of the parameter data, the groups or clusters being associated with labels dependent on features from input of the parameter data having known qualities that are related to psychological disorders; and
    means, in the Artificial Neural Network, configured for analyzing in the Artificial Neural Network the received set of parameter data by:
    (i) determining, dependent on the set of parameter data, a response value that is indicative of the distance between the received set of parameter data and the groups or clusters;
    (ii) determining, dependent on the response value, a group or cluster that is proximate to the response value;
    (iii) outputting the label of the determined group or cluster as a classification of a feature in the parameter data related to psychological disorders;
    thereby outputting an indication of the presence or absence of the psychological condition.

* * * * *